(12) United States Patent
Jager-Lezer et al.

(10) Patent No.: US 7,030,985 B2
(45) Date of Patent: *Apr. 18, 2006

(54) COLORED TRANSPARENT OR TRANSLUCENT COSMETIC COMPOSITION

(75) Inventors: Nathalie Jager-Lezer, Bourg-la-Reine (FR); Jean-Christophe Simon, Paris (FR)

(73) Assignee: L'Oréal, Paris (FR)

( * ) Notice: Subject to any disclaimer, the term of this patent is extended or adjusted under 35 U.S.C. 154(b) by 221 days.

This patent is subject to a terminal disclaimer.

(21) Appl. No.: 10/203,375

(22) PCT Filed: Dec. 11, 2001

(86) PCT No.: PCT/FR01/03937

§ 371 (c)(1),
(2), (4) Date: Aug. 9, 2002

(87) PCT Pub. No.: WO02/47627

PCT Pub. Date: Jun. 20, 2002

(65) Prior Publication Data

US 2003/0026772 A1    Feb. 6, 2003

(30) Foreign Application Priority Data

Dec. 12, 2000  (FR) .................. 00/16178

(51) Int. Cl.
G01J 3/46 (2006.01)
G01N 21/25 (2006.01)
A61K 6/00 (2006.01)

(52) U.S. Cl. .............. 356/402; 356/409; 356/432; 424/401; 424/61; 424/63; 424/64; 424/69; 424/70.7; 436/8

(58) Field of Classification Search .............. 356/402, 356/408, 409, 425, 432–434; 424/401, 61, 424/63, 64, 69, 70.7; 436/8, 46, 173
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway |
| 3,141,787 A | 7/1964 | Goetze et al. |
| 3,148,125 A | 9/1964 | Strianse et al. |
| 3,156,572 A | 11/1964 | Carlick et al. |
| 3,157,681 A | 11/1964 | Fischer |
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. ......... 424/64 |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A * | 4/1979 | Barnett et al. ........... 514/772.6 |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,367,390 A | 1/1983 | Balleys et al. |
| 4,376,194 A | 3/1983 | Tanaka et al. |
| 4,387,090 A | 6/1983 | Bolich, Jr. |
| 4,438,240 A | 3/1984 | Tanaka et al. |

(Continued)

FOREIGN PATENT DOCUMENTS

CA    2003346    5/1990

(Continued)

OTHER PUBLICATIONS

Bangham, A.D. et al. Diffusion of Univalent Ions across the Lamellae of Swollen Phospholipids, Journal of Molecular Biology, pp. 238-252, vol. 13, Aug. to Oct. 1965.

(Continued)

*Primary Examiner*—Hwa (Andrew) Lee
*Assistant Examiner*—Roy M. Punnoose
(74) *Attorney, Agent, or Firm*—Finnegan Henderson Farabow Garrett & Dunner, L.L.P.

(57) ABSTRACT

The invention relates to a transparent or translucent colored cosmetic composition for making up the skin, lips and superficial body growths comprising a transparent or translucent cosmetic base and at least one coloring agent in an amount such that the transmission of a 10 μm layer of the final composition, measured at the wavelength of the maximum of one of the absorption peaks of the coloring agent, is between 20% and 80%.

25 Claims, No Drawings

U.S. PATENT DOCUMENTS

| | | |
|---|---|---|
| 4,466,936 A | 8/1984 | Schapel |
| 4,536,405 A | 8/1985 | Nara et al. |
| 4,552,693 A | 11/1985 | Hussain et al. |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,724,137 A | 2/1988 | Hoppe et al. |
| 4,769,285 A | 9/1988 | Rasmussen |
| 4,806,338 A | 2/1989 | Smith |
| 4,806,345 A | 2/1989 | Bhattacharyya |
| 4,820,765 A | 4/1989 | Whyzmuzis |
| 4,822,601 A * | 4/1989 | Goode et al. .................. 424/59 |
| 4,871,536 A | 10/1989 | Arraudeau et al. |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr |
| 5,073,364 A | 12/1991 | Giezendanner et al. |
| 5,085,859 A | 2/1992 | Halloran et al. |
| 5,102,656 A | 4/1992 | Kasat |
| 5,166,355 A | 11/1992 | Leistner et al. |
| 5,186,318 A | 2/1993 | Oestreich et al. |
| 5,196,260 A | 3/1993 | Dirschl et al. |
| 5,223,559 A | 6/1993 | Arraudeau et al. ........... 524/47 |
| 5,237,071 A | 8/1993 | Leistner et al. |
| 5,252,323 A | 10/1993 | Richard et al. |
| 5,268,029 A | 12/1993 | Demangeon et al. |
| 5,272,241 A | 12/1993 | Lucarelli et al. |
| 5,290,555 A * | 3/1994 | Guthauser et al. .......... 424/401 |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Ross et al. |
| 5,505,937 A | 4/1996 | Castrogiovanni et al. |
| 5,510,452 A | 4/1996 | Santhanam |
| 5,536,871 A | 7/1996 | Santhanam |
| 5,538,718 A | 7/1996 | Aul et al. |
| 5,538,793 A | 7/1996 | Inokuchi et al. |
| 5,540,853 A | 7/1996 | Trinh et al. |
| 5,585,091 A | 12/1996 | Pelzer et al. |
| 5,603,925 A | 2/1997 | Ross et al. |
| 5,605,651 A * | 2/1997 | Balzer ........................ 424/401 |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. |
| 5,679,357 A | 10/1997 | Dubief et al. |
| 5,683,817 A | 11/1997 | Kenmochi |
| 5,695,747 A | 12/1997 | Forestier et al. |
| 5,702,519 A * | 12/1997 | Nitta et al. ................. 106/442 |
| 5,719,255 A | 2/1998 | Heucher et al. |
| 5,747,625 A | 5/1998 | Furukawa et al. |
| 5,750,125 A | 5/1998 | Lahanas et al. ............. 424/401 |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. ................. 514/721 |
| 5,783,657 A | 7/1998 | Pavlin et al. |
| 5,795,565 A | 8/1998 | Eteve et al. |
| 5,800,816 A | 9/1998 | Brieva et al. |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,849,909 A | 12/1998 | Richard et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. |
| 5,882,363 A | 3/1999 | Spaulding et al. |
| 5,891,424 A | 4/1999 | Bretzler |
| 5,897,869 A | 4/1999 | Roulier et al. |
| 5,902,592 A | 5/1999 | Bara et al. |
| 5,908,631 A | 6/1999 | Arnaud et al. |
| 5,911,974 A | 6/1999 | Brieva et al. |
| 5,919,441 A | 7/1999 | Mendolia et al. |
| 5,925,337 A | 7/1999 | Arraudeau et al. |
| 5,945,095 A | 8/1999 | Mougin et al. |
| 5,945,112 A | 8/1999 | Flynn et al. |
| 5,955,060 A | 9/1999 | Huglin et al. |
| 5,959,009 A | 9/1999 | Konik et al. |
| 5,961,998 A | 10/1999 | Arnaud et al. |
| 5,962,452 A | 10/1999 | Haase et al. |
| 5,965,112 A | 10/1999 | Brieva et al. |
| 5,972,095 A | 10/1999 | Graves et al. |
| 5,972,354 A | 10/1999 | de la Poterie et al. |
| 5,972,359 A | 10/1999 | Sine et al. ................... 424/401 |
| 5,976,512 A | 11/1999 | Huber |
| 5,976,514 A | 11/1999 | Guskey et al. |
| 5,981,680 A | 11/1999 | Petroff et al. |
| 5,985,298 A | 11/1999 | Brieva et al. |
| 5,993,787 A * | 11/1999 | Sun et al. ..................... 424/59 |
| 5,998,570 A | 12/1999 | Pavlin et al. |
| 6,001,980 A | 12/1999 | Borzo et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |
| 6,051,216 A | 4/2000 | Barr et al. |
| 6,054,517 A | 4/2000 | Spaulding et al. |
| 6,060,072 A | 5/2000 | Konik et al. |
| 6,063,398 A | 5/2000 | Gueret |
| 6,066,328 A | 5/2000 | Ribier et al. |
| 6,074,654 A | 6/2000 | Drechsler et al. |
| 6,093,385 A | 7/2000 | Habeck et al. |
| 6,103,249 A | 8/2000 | Roulier et al. |
| 6,106,820 A | 8/2000 | Morrissey et al. |
| 6,111,055 A | 8/2000 | Berger et al. |
| 6,132,745 A | 10/2000 | Marchi-Lemann et al. |
| 6,156,325 A | 12/2000 | Farer et al. |
| 6,156,804 A | 12/2000 | Chevalier et al. |
| 6,159,455 A | 12/2000 | Habeck et al. |
| 6,165,454 A | 12/2000 | Patel et al. |
| 6,165,971 A | 12/2000 | Oppenlander et al. |
| 6,171,347 B1 | 1/2001 | Kunz et al. |
| 6,177,523 B1 | 1/2001 | Reich et al. |
| 6,180,117 B1 | 1/2001 | Berthiaume et al. |
| 6,180,123 B1 | 1/2001 | Mondet |
| 6,190,673 B1 | 2/2001 | Guskey et al. |
| 6,197,100 B1 | 3/2001 | Melbouci |
| 6,203,780 B1 | 3/2001 | Arnaud et al. |
| 6,203,807 B1 | 3/2001 | Lemann |
| 6,214,326 B1 | 4/2001 | Dupuis |
| 6,214,329 B1 | 4/2001 | Brieva et al. |
| 6,221,389 B1 | 4/2001 | Cannell et al. |

| | | |
|---|---|---|
| 6,224,851 B1 | 5/2001 | Bara |
| 6,242,509 B1 | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | de la Poterie et al. |
| 6,264,933 B1 | 7/2001 | Bodelin et al. |
| 6,268,466 B1 | 7/2001 | MacQueen et al. |
| 6,280,846 B1 | 8/2001 | Darby et al. |
| 6,287,552 B1 | 9/2001 | Tournilhac et al. |
| 6,325,994 B1 | 12/2001 | Collin et al. |
| 6,348,563 B1 | 2/2002 | Fukuda et al. |
| 6,361,764 B1 | 3/2002 | Richard et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,399,080 B1 | 6/2002 | Bara |
| 6,399,081 B1 | 6/2002 | Nakanishi et al. |
| 6,402,408 B1 | 6/2002 | Ferrari |
| 6,423,306 B1 | 7/2002 | Caes et al. |
| 6,423,324 B1 | 7/2002 | Murphy et al. |
| 6,428,773 B1 * | 8/2002 | Oko et al. .................. 424/63 |
| 6,432,391 B1 | 8/2002 | Bara |
| 6,447,759 B1 * | 9/2002 | Noguchi et al. ............. 424/59 |
| 6,469,131 B1 | 10/2002 | Lawson et al. |
| 6,475,500 B1 | 11/2002 | Vatter et al. |
| 6,479,686 B1 | 11/2002 | Nakanishi et al. |
| 6,482,400 B1 | 11/2002 | Collin |
| 6,491,931 B1 | 12/2002 | Collin |
| 6,497,861 B1 | 12/2002 | Wang et al. |
| 6,503,522 B1 | 1/2003 | Lawson et al. |
| 6,506,716 B1 | 1/2003 | Delplancke et al. |
| 6,545,174 B1 | 4/2003 | Habeck et al. |
| 6,552,160 B1 | 4/2003 | Pavlin |
| 6,649,173 B1 | 11/2003 | Arnaud et al. |
| 6,682,748 B1 | 1/2004 | De La Poterie et al. |
| 6,716,420 B1 | 4/2004 | Feng et al. |
| 6,726,917 B1 | 4/2004 | Kanji et al. |
| 6,761,881 B1 * | 7/2004 | Bara ..................... 424/63 |
| 6,875,245 B1 | 4/2005 | Pavlin |
| 2001/0014312 A1 | 8/2001 | Nakanishi et al. |
| 2001/0014313 A1 | 8/2001 | Roulier et al. |
| 2001/0028887 A1 | 10/2001 | Douin et al. |
| 2001/0031280 A1 | 10/2001 | Ferrari et al. |
| 2001/0033846 A1 | 10/2001 | Roulier et al. |
| 2002/0010179 A1 | 1/2002 | Richard et al. |
| 2002/0044918 A1 | 4/2002 | Bara |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0107314 A1 | 8/2002 | Pinzon et al. |
| 2002/0111330 A1 | 8/2002 | Pinzon et al. |
| 2002/0114771 A1 | 8/2002 | Nakanishi |
| 2002/0114773 A1 | 8/2002 | Kanji et al. |
| 2002/0119171 A1 | 8/2002 | Gruning et al. |
| 2002/0120036 A1 | 8/2002 | Pinzon et al. |
| 2002/0122781 A1 | 9/2002 | Pinzon et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2002/0168335 A1 | 11/2002 | Collin |
| 2002/0172696 A1 | 11/2002 | Ferrari |
| 2002/0189030 A1 | 12/2002 | Collin |
| 2002/0192168 A1 | 12/2002 | Blin et al. |
| 2003/0012764 A1 | 1/2003 | Collin |
| 2003/0026772 A1 | 2/2003 | Jager-Lezer et al. |
| 2003/0044367 A1 | 3/2003 | Simon et al. |
| 2003/0086883 A1 | 5/2003 | Feng et al. |
| 2003/0147837 A1 | 8/2003 | Cavazzuti et al. |
| 2003/0161807 A1 | 8/2003 | Lemann |
| 2003/0161848 A1 | 8/2003 | Ferrari et al. |
| 2003/0185780 A1 | 10/2003 | Ferrari et al. |
| 2003/0198613 A1 | 10/2003 | Feng et al. |
| 2004/0013625 A1 | 1/2004 | Kanji |
| 2004/0028636 A1 | 2/2004 | Collin |
| 2004/0042980 A1 | 3/2004 | Kanji et al. |
| 2004/0086478 A1 | 5/2004 | Ferrari |
| 2004/0091510 A1 | 5/2004 | Feng et al. |
| 2004/0126401 A1 | 7/2004 | Collin |
| 2004/0166076 A1 | 8/2004 | Ferrari et al. |
| 2004/0166133 A1 | 8/2004 | Cavazzuti et al. |

FOREIGN PATENT DOCUMENTS

| | | |
|---|---|---|
| CA | 1319306 | 6/1993 |
| DE | 38 39 136 A1 | 5/1990 |
| DE | 38 43 892 A1 | 6/1990 |
| DE | 42 08 297 A1 | 9/1993 |
| DE | 42 34 886 A1 | 4/1994 |
| DE | 195 43 988 A1 | 5/1997 |
| DE | 197 07 309 | 8/1998 |
| DE | 197 26 184 A1 | 12/1998 |
| DE | 197 50 246 A1 | 5/1999 |
| DE | 197 55 649 A1 | 6/1999 |
| DE | 198 55 649 A1 | 6/2000 |
| DE | 199 51 010 A1 | 4/2001 |
| EP | 0 169 997 B1 | 2/1986 |
| EP | 0 295 886 B1 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 507 692 A1 | 10/1992 |
| EP | 0 517 104 B1 | 12/1992 |
| EP | 0 518 772 A1 | 12/1992 |
| EP | 0 518 773 A1 | 12/1992 |
| EP | 0 557 196 A1 | 8/1993 |
| EP | 0 570 838 B1 | 11/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 669 323 A1 | 8/1995 |
| EP | 0 673 642 B1 | 9/1995 |
| EP | 0 708 114 A1 | 4/1996 |
| EP | 0 749 746 A1 | 12/1996 |
| EP | 0 749 747 A1 | 12/1996 |
| EP | 0 749 748 A1 | 12/1996 |
| EP | 0 775 483 A1 | 5/1997 |
| EP | 0 775 698 A1 | 5/1997 |
| EP | 0 790 243 A1 | 8/1997 |
| EP | 0 796 851 A1 | 9/1997 |
| EP | 0 797 976 A2 | 10/1997 |
| EP | 0 820 764 A1 | 1/1998 |
| EP | 0 847 752 A1 | 6/1998 |
| EP | 0 863 145 A2 | 9/1998 |
| EP | 0 877 063 B1 | 11/1998 |
| EP | 0 878 469 A1 | 11/1998 |
| EP | 0 879 592 A2 | 11/1998 |
| EP | 0 887 073 A1 | 12/1998 |
| EP | 0 893 119 B1 | 1/1999 |
| EP | 0 923 928 A1 | 6/1999 |
| EP | 0 925 780 A1 | 6/1999 |
| EP | 0 928 608 A2 | 7/1999 |
| EP | 0 930 058 B1 | 7/1999 |
| EP | 0 930 060 A1 | 7/1999 |
| EP | 0 933 376 A2 | 8/1999 |
| EP | 0 943 340 A1 | 9/1999 |
| EP | 0 958 804 A2 | 11/1999 |
| EP | 0 958 805 A2 | 11/1999 |
| EP | 0 958 811 A1 | 11/1999 |
| EP | 0 959 066 A2 | 11/1999 |
| EP | 0 959 091 A1 | 11/1999 |
| EP | 0 967 200 A1 | 12/1999 |
| EP | 0 976 390 A1 | 2/2000 |

| | | | | | | |
|---|---|---|---|---|---|---|
| EP | 0 984 025 A2 | 3/2000 | | JP | 09/20631 | 1/1997 |
| EP | 1 002 514 A1 | 5/2000 | | JP | 09/255560 | 9/1997 |
| EP | 1 031 342 A1 | 8/2000 | | JP | 09/295922 | 11/1997 |
| EP | 1 044 676 A2 | 10/2000 | | JP | 10/007527 | 1/1998 |
| EP | 1 048 282 A1 | 11/2000 | | JP | 10/120903 | 5/1998 |
| EP | 1 053 742 A1 | 11/2000 | | JP | 10/212213 | 8/1998 |
| EP | 1 062 944 A1 | 12/2000 | | JP | 10/259344 | 9/1998 |
| EP | 1 062 959 A1 | 12/2000 | | JP | 11/106216 | 4/1999 |
| EP | 1 064 919 A1 | 1/2001 | | JP | 11/335228 | 12/1999 |
| EP | 1 064 920 A1 | 1/2001 | | JP | 11/335242 | 12/1999 |
| EP | 1 066 814 A1 | 1/2001 | | JP | 11/335254 | 12/1999 |
| EP | 1 068 854 A1 | 1/2001 | | JP | 2000038314 A | 2/2000 |
| EP | 1 068 855 A1 | 1/2001 | | JP | 2000038316 A | 2/2000 |
| EP | 1 068 856 A1 | 1/2001 | | JP | 2000038317 A | 2/2000 |
| EP | 1 086 945 A1 | 3/2001 | | JP | 2000038321 A | 2/2000 |
| EP | 1 090 627 B1 | 4/2001 | | JP | 2000086427 A | 3/2000 |
| EP | 1 095 959 A2 | 5/2001 | | JP | 2000086429 A | 3/2000 |
| EP | 1 114 636 A1 | 7/2001 | | JP | 2000086438 A | 3/2000 |
| EP | 1 213 011 A1 | 6/2002 | | WO | WO 86/04916 | 8/1986 |
| EP | 1 213 316 A2 | 6/2002 | | WO | WO 87/03783 | 7/1987 |
| FR | 1 529 329 | 5/1968 | | WO | WO 91/12793 | 9/1991 |
| FR | 2 232 303 | 1/1975 | | WO | WO 93/04665 | 3/1993 |
| FR | 2 315 991 | 1/1977 | | WO | WO 93/21763 | 11/1993 |
| FR | 2 416 008 | 8/1979 | | WO | WO 93/23008 | 11/1993 |
| FR | 2 674 126 | 9/1992 | | WO | WO 94/18261 | 8/1994 |
| FR | 2 785 179 | 5/2000 | | WO | WO 94/21233 | 9/1994 |
| FR | 2 796 270 | 1/2001 | | WO | WO 95/15741 | 6/1995 |
| FR | 2 796 271 | 1/2001 | | WO | WO 95/24887 | 9/1995 |
| FR | 2 796 272 | 1/2001 | | WO | WO 95/33000 | 12/1995 |
| FR | 2 796 273 | 1/2001 | | WO | WO 96/15761 | 5/1996 |
| FR | 2 796 276 | 1/2001 | | WO | WO 96/40044 | 12/1996 |
| FR | 2 796 550 | 1/2001 | | WO | WO 97/17057 | 5/1997 |
| FR | 2 802 806 | 6/2001 | | WO | WO 97/36573 | 10/1997 |
| FR | 2 804 014 | 7/2001 | | WO | WO 98/17243 | 4/1998 |
| FR | 2 804 017 | 7/2001 | | WO | WO 98/17705 | 4/1998 |
| FR | 2 804 018 | 7/2001 | | WO | WO 98/22078 | 5/1998 |
| FR | 2 810 562 | 12/2001 | | WO | WO 98/25922 | 6/1998 |
| FR | 2 811 225 | 1/2002 | | WO | WO 98/27162 | 6/1998 |
| FR | 2 811 552 | 1/2002 | | WO | WO 98/42298 | 10/1998 |
| FR | 2 816 506 | 5/2002 | | WO | WO 98/47470 | 10/1998 |
| FR | 2 817 739 | 6/2002 | | WO | WO 98/52534 | 11/1998 |
| FR | 2 817 740 | 6/2002 | | WO | WO 98/58623 | 12/1998 |
| FR | 2 817 742 | 6/2002 | | WO | WO99/24002 | 5/1999 |
| FR | 2 817 743 | 6/2002 | | WO | WO 00/27350 | 5/2000 |
| FR | 2 819 399 | 7/2002 | | WO | WO 00/40216 | 7/2000 |
| FR | 2 819 400 | 7/2002 | | WO | WO 00/61080 | 10/2000 |
| FR | 2 819 402 | 7/2002 | | WO | WO 00/61081 | 10/2000 |
| GB | 1 117 129 | 6/1968 | | WO | WO 00/74519 A2 | 12/2000 |
| GB | 1 194 901 | 6/1970 | | WO | WO 01/51020 A1 | 7/2001 |
| GB | 1 194 902 | 6/1970 | | WO | WO 01/52799 A1 | 7/2001 |
| GB | 1 220 069 | 1/1971 | | WO | WO 01/97758 A2 | 12/2001 |
| GB | 1 273 004 | 5/1972 | | WO | WO 01/97773 A1 | 12/2001 |
| GB | 1 444 204 | 7/1976 | | WO | WO 02/03932 A2 | 1/2002 |
| GB | 1 539 625 | 1/1979 | | WO | WO 02/03935 A2 | 1/2002 |
| GB | 2 014 852 A | 9/1979 | | WO | WO 02/03950 A2 | 1/2002 |
| GB | 2 021 411 A | 12/1979 | | WO | WO 02/03951 A2 | 1/2002 |
| GB | 2 147 305 A | 5/1985 | | WO | WO 02/47605 A2 | 6/2002 |
| GB | 2 196 978 A | 5/1988 | | WO | WO 02/47606 A2 | 6/2002 |
| JP | 50/58242 | 5/1975 | | WO | WO 02/47608 A2 | 6/2002 |
| JP | 53/043577 | 4/1978 | | WO | WO 02/47619 A2 | 6/2002 |
| JP | 56/123909 | 9/1981 | | WO | WO 02/47620 A2 | 6/2002 |
| JP | 56/166276 | 12/1981 | | WO | WO 02/47622 A2 | 6/2002 |
| JP | 61/065809 | 4/1986 | | WO | WO 02/47627 A1 | 6/2002 |
| JP | 62/061911 | 3/1987 | | WO | WO 02/47629 A1 | 6/2002 |
| JP | 02/127568 | 5/1990 | | WO | WO 02/47630 A1 | 6/2002 |
| JP | 02/200612 | 8/1990 | | WO | WO 02/47658 A2 | 6/2002 |
| JP | 02/207014 | 8/1990 | | WO | WO 02/49583 A1 | 6/2002 |
| JP | 02/216279 | 8/1990 | | WO | WO 02/49601 A1 | 6/2002 |
| JP | 03/014683 | 1/1991 | | WO | WO 02/055030 A2 | 7/2002 |
| JP | 04346909 | 12/1993 | | WO | WO 02/055031 A1 | 7/2002 |
| JP | 07/179795 | 7/1995 | | WO | WO 02/056845 A1 | 7/2002 |
| JP | 07/267827 | 10/1995 | | WO | WO 02/056847 A1 | 7/2002 |
| JP | 08/225316 | 9/1996 | | WO | WO 02/056848 A1 | 7/2002 |

| | | | |
|---|---|---|---|
| WO | WO 02/092047 A1 | 11/2002 | |
| WO | WO 02/092663 A1 | 11/2002 | |
| WO | WO 02/102322 A2 | 12/2002 | |
| WO | WO 05/013887 A2 | 2/2005 | |

OTHER PUBLICATIONS

Bush Boake Allen, Inc., Uniclear Formulations, dated Oct. 13, 1998.
Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-117.
Co-Pending U.S. Appl. No. 09/618,032; issued as U.S. Patent No. 6,402,408 on Jun. 11, 2002, Title: Composition Containing a Liquid Fatty Phase Gelled With a Polyamide Containing Ester End Groups Inventor: Véronique Ferrari U.S. Filing Date: Jul. 17, 2000.
Co-Pending U.S. Appl. No. 09/618,066; Title: Compositions in Rigid Form Structured With a Polymer Inventors: Véronique Ferrari and Pascal Simon, U.S. Filing Date: Jul. 17, 2000.
Co-Pending U.S. Appl. No. 09/685,577; Title: Compositions in Rigid Form Structured With a Polymer Inventors: Véronique Ferrari and Pascal Simon U.S. Filing Date: Oct. 11, 2000.
Co-Pending U.S. Appl. No. 09/685,578; Title: Composition Containing a Liquid Fatty Phase Gelled With a Polyamide Containing Ester End Groups Inventor: Véronique Ferrari U.S. Filing Date: CIP filed Oct. 11, 2000.
Co-Pending U.S. Appl. No. 09/733,896; Title: Compositions Containing Heteropolymers and Oil-Soluble Polymers and Methods of Using Same Inventors: Carlos Pinzon and Paul Thau U.S. Filing Date: Dec. 12, 2000.
Co-Pending U.S. Appl. No. 09/733,897; Title: Compositions Containing Heteropolymers and Methods of Using Same Inventors: Carlos Pinzon and Paul Thau U.S. Filing Date: Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau U.S. Filing Date: Dec. 12, 2000.
Co-Pending U.S. Appl. No. 09/733,899; Title: Cosmetic Compositions Containing at Least One Hetero Polymer and at Least One Film-Forming Silicone Resin and Methods of Using Inventors: Mohamed Kanji et al. U.S. Filing Date: Dec. 12, 2000.
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau U.S. Filing Date: Dec. 12, 2000.
Co-Pending U.S. Appl. No. 09/749,036; Title: Composition Comprising at Least One Hetero Polymer and at Least One Pasty Fatty Substance and Methods for Use Inventors: Véronique Ferrari et al. U.S. Filing Date: Dec. 28, 2000.
Co-Pending U.S. Appl. No. 09/899,909, issued as U.S. Patent No. 6,432,391 on Aug. 13, 2002, Title: Transparent Scented Solid Cosmetic Composition U.S. Filing Date: Jul. 9, 2001.
Co-Pending U.S. Appl. No. 09/937,314; Title: Transfer-Free Composition Structured in the Stiff Form by a Polymer U.S. Filing Date: Sep. 24, 2001.
Co-Pending U.S. Appl. No. 09/971,028, issued as U.S. Patent No. 6,716,420 on Apr. 6, 2004; Title: Methods of Dispersing at Least One Coloring Agent Using at Least One Heteropolymer U.S. Filing Date: Oct. 5, 2001.
Co-Pending U.S. Appl. No. 10/012,029; Title: Cosmetic Composition Comprising a Polymer Blend U.S. Filing Date: Dec. 11, 2001.
Co-Pending U.S. Appl. No. 10/012,051; Title: Use of a Polymer for Obtaining an Express Make-Up of Keratin Materials U.S. Filing Date: Dec. 11, 2001.
Co-Pending U.S. Appl. No. 10/012,052; Title: Cosmetic Composition Comprising a Wax and a Polymer U.S. Filing Date: Dec. 11, 2001.
Co-Pending U.S. Appl. No. 10/046,568; Title: Nail Polish Composition Comprising a Polymer U.S. Filing Date: Jan. 16, 2002.
Co-Pending U.S. Appl. No. 10/047,987, Title: Cosmetic Composition Containing a Polymer and a Fluoro Oil U.S. Filing Date: Jan. 17, 2002.
Co-Pending U.S. Appl. No. 10/129,377; Title: Compositions Structured With a Polymer Containing a Heteroatom and an Organogelator U.S. Filing Date: May 3, 2002.
Co-Pending U.S. Appl. No. 10/182,830; Title: Cosmetic Composition Comprising Hetero Polymers and a Solid Substance and Method of Using Same U.S. Filing Date: Aug. 2, 2002.
Co-Pending U.S. Appl. No. 10/198,931, Title: Compositions Comprising at Least One Heteropolymer and Fibers, and Methods of Using the Same U.S. Filing Date: Jul. 22, 2002.
Co-Pending U.S. Appl. No. 10/203,018; Title: Composition Comprising at Least One Hetero Polymer and at Least One Inert Filler and Methods for Use U.S. Filing Date: Aug. 5, 2002.
Co-Pending U.S. Appl. No. 10/203,254; Title: Cosmetic Compositions Containing at Least One Heteropolymer and at Least One Gelling Agent and Methods of Using the Same U.S. Filing Date: Aug. 7, 2002.
Co-Pending U.S. Appl. No. 10/203,374, Title: Method for Making a Coloured Make-Up Cosmetic Composition With Controlled Transmittance U.S. Filing Date: Aug. 9, 2002.
Co-Pending U.S. Appl. No. 10/203,375, Title: Transparent or Translucent Colored Cosmetic Composition U.S. Filing Date: Aug. 9, 2002.
Co-Pending U.S. Appl. No. 10/312,083, Title: Solid Emulsion Containing a Liquid Fatty Phase Structured With a Polymer U.S. Filing Date: Dec. 23, 2002.
Co-Pending U.S. Appl. No. 10/413,217, Title: Methods of Dispersing at Least One Coloring Agent Using at Least One Heteropolymer U.S. Filing Date: Apr. 15, 2003.
Co-Pending U.S. Appl. No. 10/450,108, Title: Cosmetic Composition Comprising a Polymer and Fibres U.S. Filing Date: Jun. 11, 2003.
Co-Pending U.S. Appl. No. 10/459,636, Title: Cosmetic Emulsions Containing at Least One Hetero Polymer and at Least One Sunscreen and Methods of Using the Same U.S. Filing Date: Jun. 12, 2003.
Co-Pending U.S. Appl. No. 10/466,166, Title: Cosmetic Composition Comprising a Mixture of Polymers U.S. Filing Date: Jul. 14, 2003.
Co-Pending U.S. Appl. No. 10/494,864; Title: Composition Containing an Amino Acid N-Acylated Ester and a Polyamide-Structured UV Filter U.S. Filing Date: Nov. 23, 2004.
Co-Pending U.S. Appl. No. 10/618,315, Title: Cosmetic Compositions Comprising a Structuring Agent, Silicone Powder and Swelling Agent U.S. Filing Date: Jun. 11, 2003.

Co-Pending U.S. Appl. No. 10/699,780, Title: Methods of Dispersing at Least One Coloring Agent Using at Least One Heteropolymer U.S. Filing Date: Nov. 4, 2003.
Co-Pending U.S. Appl. No. 10/746,612, Title: Cosmetic Compositions Comprising a Structuring Agent, Silicone Powder and Swelling Agent U.S. Filing Date: Dec. 22, 2003.
Co-Pending U.S. Appl. No. 10/747,412, Title: Cosmetic Emulsions Containing at Least One Hetero Polymer and at Least One Sunscreen and Methods of Using the Same U.S. Filing Date: Dec. 22, 2003.
Co-Pending U.S. Appl. No. 10/787,440, Title: Composition Comprising at Least One Hetero Polymer and at Least One Inert Filler and Methods for Use U.S. Filing Date: Feb. 27, 2004.
Co-Pending U.S. Appl. No. 10/787,441, Title: Cosmetic Composition Comprising Hetero Polymers and a Solid Substance and Method of Using Same U.S. Filing Date: Feb. 27, 2004.
Co-Pending U.S. Appl. No. 10/918,579, Title: Compositions Containing Heteropolymers and Oilsoluble Esters and Methods of Using Same U.S. Filing Date: Aug. 16, 2004.
Co-Pending U.S. Appl. No. 10/990,475, Title: Use of a Polymer for Obtaining an Express Make-Up of Keratin Materials U.S. Filing Date: Nov. 18, 2004.
Co-Pending U.S. Appl. No. 10/993,430, Title: Cosmetic Composition Comprising a Polymer Blend, U.S. Filing Date: Nov. 22, 2004.
Co-Pending U.S. Appl. No. 10/993,431, Title: A Transfer-Free Composition Structured in Rigid Form by a Polymer, U.S. Filing Date: Nov. 22, 2004.
Co-Pending U.S. Appl. No. 11/019,382; Title: Cosmetic Composition Comprising Two Different Hetero Polymers and Method of Using Same, U.S. Filing Date: Dec. 23, 2004.
English Language Abstract of FR 2 804 014 from esp@cenet.
English Language Abstract of FR 2 817 742 from esp@cenet.
English language abstract of JP 53/043577 from Patent Abstracts of Japan.
English language abstract of JP 56/123909 from Patent Abstracts of Japan.
English language abstract of JP 56/166276 from Patent Abstracts of Japan.
English language abstract of JP 78/043577 from Patent Abstracts of Japan.
English language DERWENT abstract of DE 195 43 988 A1.
English language DERWENT abstract of DE 197 07 309 A1.
English language DERWENT abstract of DE 197 26 184.
English language DERWENT abstract of DE 197 50 246 A1.
English language DERWENT abstract of DE 197 55 649 A1.
English language DERWENT abstract of DE 198 55 649 A1.
English language DERWENT abstract of DE 199 51 010 A1.
English language DERWENT abstract of DE 38 39 136 A1.
English language DERWENT abstract of DE 38 43 892 A1.
English language DERWENT abstract of DE 42 08 297 A1.
English language DERWENT abstract of DE 42 34 886 A1.
English language DERWENT abstract of EP 0 169 997 B.
English language DERWENT abstract of EP 0 507 692 A1.
English language DERWENT abstract of EP 0 518 772 A1.
English language DERWENT abstract of EP 0 518 773 A1.
English language DERWENT abstract of EP 0 557 196 A1.
English language DERWENT abstract of EP 0 609 132 B1.
English language DERWENT abstract of EP 0 669 323 A1.
English language DERWENT abstract of EP 0 749 746 A1.
English language DERWENT abstract of EP 0 749 747 A1.
English language DERWENT abstract of EP 0 749 748 A1.
English language DERWENT abstract of EP 0 775 483 A1.
English language DERWENT abstract of EP 0 775 698 A1.
English language DERWENT abstract of EP 0 790 243 A1.
English language DERWENT abstract of EP 0 820 764 A1.
English language DERWENT abstract of EP 0 847 752 A1.
English language DERWENT abstract of EP 0 863 145 A2.
English language DERWENT abstract of EP 0 878 469 A1.
English language DERWENT abstract of EP 0 879 592 A2.
English language DERWENT abstract of EP 0 887 073 A1.
English language DERWENT abstract of EP 0 923 928 A1.
English language DERWENT abstract of EP 0 925 780 A1.
English language DERWENT abstract of EP 0 930 058 B1.
English language DERWENT abstract of EP 0 930 060 A1.
English language DERWENT abstract of EP 0 943 340 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 967 200 A1.
English language DERWENT abstract of EP 0 976 390 A1.
English language DERWENT abstract of EP 1 002 514 A1.
English language DERWENT abstract of EP 1 031 342 A1.
English language DERWENT abstract of EP 1 048 282 A1.
English language DERWENT abstract of EP 1 053 742 A1.
English language DERWENT abstract of EP 1 064 919 A1.
English language DERWENT abstract of EP 1 064 920 A1.
English language DERWENT abstract of EP 1 066 814 a1.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of EP 1 114 636 A1.
English language DERWENT abstract of FR 2 232 303.
English language DERWENT abstract of FR 2 315 991.
English language DERWENT abstract of FR 2 416 008.
English language DERWENT abstract of FR 2 674 126.
English language DERWENT abstract of FR 2 785 179.
English language DERWENT abstract of FR 2 796 270.
English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 796 550.
English language DERWENT abstract of FR 2 802 806.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 811 552.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 02/200612.
English language DERWENT abstract of JP 04/346909.
English language DERWENT abstract of JP 09/255560.
English language DERWENT abstract of JP 10/007527.
English language DERWENT abstract of JP 10/120903.
English language DERWENT abstract of JP 10/212213.
English language DERWENT abstract of JP 10/259344.
English language DERWENT abstract of JP 11/106216.

English language DERWENT abstract of JP 11/335228.
English language DERWENT abstract of JP 11/335242.
English language DERWENT abstract of JP 11/335254.
English language DERWENT abstract of JP 2/127568.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 2216279.
English language DERWENT abstract of JP 3014683.
English language DERWENT abstract of JP 61065809.
English language DERWENT abstract of JP 62061911.
English language DERWENT abstract of JP 7179795.
English language DERWENT abstract of JP 7267827.
English language DERWENT abstract of JP 8225316.
English language DERWENT abstract of JP 920631.
English language DERWENT abstract of JP 9295922.
English language DERWENT abstract of WO 01/97773.
English language DERWENT abstract of WO 02/056847.
English language DERWENT abstract of WO 02/056848.
English language DERWENT abstract of WO 02/47622.
English language DERWENT abstract of WO 02/47629.
English language DERWENT abstract of WO 02/47630.
English language DERWENT abstract of WO 86/04916.
English language DERWENT abstract of WO 93/04665.
English language DERWENT abstract of WO 98/25922.
Estee Lauder MagnaScopic Maximum Volume mascara product packaging, believed to have first been sold in 2003.
Estee Lauder' Amended Answer and Counterclaims, dated Apr. 21, 2005, in the on-going litigation L'Oreal S.A., et al., v. The Estee Lauder Companies Inc., et al., Civil Action No. 04-1660 (D.N.J.).
Estee Lauder's Response to Plaintiff's First Set of Interrogatories (Nos. 1-6), dated Sep. 27, 2004, in the on-going litigation L'Oreal S.A., et al. v. The Estee Lauder Companies Inc., et al., Civil Action No. 04-1660 (D.N.J.).
Estee Lauder's Response to Plaintiff's Third Set of Interrogatories (Nos. 8-13), dated Jun. 21, 2005, in the on-going litigation L'Oreal S.A., et al. v. The Estee Lauder Companies Inc., et al., Civil Action No. 04-1660 (D.N.J.).
French Search Report in FR 0000920 (priority document for PCT/FR01/00229), dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
French Search Report in FR 0016164, dated Sep. 6, 2001.
French Search Report in FR 0016180, dated Oct. 16, 2001.
French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), pp. 1-32.
Harry's Cosmeticology 375-383 (J.B. Wilkinson & R.J. Moore eds., Chemical Pub. 7th ed. 1982).
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939, dated Apr. 15, 2002.
International Search Report in PCT/FR01/03940, dated Mar. 13, 2002.
International Search Report in PCT/FR01/03945, dated May 31, 2002.
International Search Report in PCT/FR02/00129, dated Jun. 14, 2002.
International Search Report in PCT/FR02/00144, dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Oct. 4, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47454, dated Aug. 29, 2002.
International Search Report in PCT/US 01/47459, dated Feb. 6, 2003.
International Search Report in PCT/US 01/47496, dated Feb. 26, 2003.
International Search Report in PCT/US 01/47497, dated Aug. 30, 2002.
International Search Report in PCT/US 01/47499, dated Aug. 8, 2002.
International Search Report in PCT/US 03/41618, dated Mar. 11, 2005.
International Search Report in PCT/US04/01071, dated Feb. 22, 2005.
Kenji Hanabusa et al., Easy Preparation and Prominent Gelation of New Gelator Based on L-Lysine, 2000 Chem. Letters, 1070-1071.
Kenji Hanabusa et al., Prominent Gelation and Chiral Aggregation of Alkylamides Derived from trans-1,2-Diaminocyclohexane, Angew. Chem. Int. Ed. Engl. 1996, 35, No. 17, 1949-1951.
Kenji Hanabusa et al., Terephthaloyl Derivatives as New Gelators; Excellent Gelation Ability and Remarkable Increase of Gel Strength by Adding Polymers, 1999 Chemistry Letters 767-768.

Kirk-Othmer, "Encyclopedia of Chemical Technology", Third Edition, vol. 22, John Wiley & Sons, 1983, pp. 332-342.
McCutcheon's vol. 1: Emulsifiers & Detergents, North American Edition MC Publishing Co., Glen Rock NJ (1993), pp. 272-273.
Milan Jokic et al., A Novel Type of Small Organic Gelators: Bis(Amino Acid) Oxalyl Amides, 1995 J. Chem. Soc., Chem. Commun., 1723-1724.
Co-pending U.S. Appl. No. 09/618,066 filed Dec. 21, 2001.
Co-pending U.S. Appl. No. 09/618,066 filed Jul. 15, 2002.
Co-pending U.S. Appl. No. 09/618,066 filed Jul. 16, 2003.
Co-pending U.S. Appl. No. 09/618,066 filed Nov. 19, 2003.
Co-pending U.S. Appl. No. 09/685,577 filed Aug. 11, 2004.
Co-pending U.S. Appl. No. 09/685,577 filed Jul. 15, 2002.
Co-pending U.S. Appl. No. 09/685,577 filed Jul. 16, 2003.
Co-pending U.S. Appl. No. 09/685,577 filed Nov. 19, 2003.
Co-pending U.S. Appl. No. 09/685,578 filed Aug. 11, 2004.
Co-pending U.S. Appl. No. 09/685,578 filed Feb. 8, 2005.
Co-pending U.S. Appl. No. 09/685,578 filed May 7, 2003.
Co-pending U.S. Appl. No. 09/685,578 filed Nov. 19, 2003.
Co-pending U.S. Appl. No. 09/733,896 filed Jan. 28, 2003.
Co-pending U.S. Appl. No. 09/733,896 filed Jul. 13, 2005.
Co-pending U.S. Appl. No. 09/733,896 filed Jul. 19, 2002.
Co-pending U.S. Appl. No. 09/733,896 filed Nov. 18, 2003.
Co-pending U.S. Appl. No. 09/733,897 filed Apr. 15, 2002.
Co-pending U.S. Appl. No. 09/733,897 filed Apr. 23, 2003.
Co-pending U.S. Appl. No. 09/733,897 filed Aug. 29, 2002.
Co-pending U.S. Appl. No. 09/733,897 filed May 6, 2004.
Co-pending U.S. Appl. No. 09/733,898 filed Apr. 25, 2005.
Co-pending U.S. Appl. No. 09/733,898 filed Apr. 29, 2003.
Co-pending U.S. Appl. No. 09/733,898 filed Aug. 28, 2002.
Co-pending U.S. Appl. No. 09/733,898 filed Dec. 23, 2003.
Co-pending U.S. Appl. No. 09/733,899 filed Apr. 7, 2004.
Co-pending U.S. Appl. No. 09/733,899 filed Apr. 9, 2003.
Co-pending U.S. Appl. No. 09/733,899 filed May 3, 2005.
Co-pending U.S. Appl. No. 09/733,899 filed Sep. 22, 2004.
Co-pending U.S. Appl. No. 09/733,900 filed Apr. 7, 2004.
Co-pending U.S. Appl. No. 09/733,900 filed Dec. 1, 2004.
Co-pending U.S. Appl. No. 09/733,900 filed Jul. 16, 2003.
Co-pending U.S. Appl. No. 09/733,900, filed Jun. 2, 2005.
Co-pending U.S. Appl. No. 09/749,036 filed Apr. 29, 2005.
Co-pending U.S. Appl. No. 09/749,036 filed Aug. 13, 2003.
Co-pending U.S. Appl. No. 09/749,036 filed Jul. 16, 2002.
Co-pending U.S. Appl. No. 09/749,036 filed May 5, 2004.
Co-pending U.S. Appl. No. 09/899,909 filed Dec. 18, 2001.
Co-pending U.S. Appl. No. 09/937,314 filed May 19, 2004.
Co-pending U.S. Appl. No. 09/971,028 filed Aug. 11, 2003.
Co-pending U.S. Appl. No. 09/971,028 filed Mar. 26, 2003.
Co-pending U.S. Appl. No. 10/012,029 filed Nov. 20, 2002.
Co-pending U.S. Appl. No. 10/012,029 filed Sep. 28, 2003.
Co-pending U.S. Appl. No. 10/012,051 filed Jan. 14, 2003.
Co-pending U.S. Appl. No. 10/012,051 filed May 14, 2004.
Co-pending U.S. Appl. No. 10/012,051 filed Oct. 3, 2003.
Co-pending U.S. Appl. No. 10/012,052 filed Aug. 9, 2004.
Co-pending U.S. Appl. No. 10/012,052 filed Nov. 6, 2003.
Co-pending U.S. Appl. No. 10/012,052, filed Jun. 3, 2005.
Co-pending U.S. Appl. No. 10/046,568 filed Dec. 30, 2003.
Co-pending U.S. Appl. No. 10/046,568 filed Jun. 12, 2003.
Co-pending U.S. Appl. No. 10/046,568 filed Nov. 5, 2002.
Co-pending U.S. Appl. No. 10/046,568 filed Sep. 22, 2004.
Co-pending U.S. Appl. No. 10/047,987 filed Dec. 11, 2003.
Co-pending U.S. Appl. No. 10/047,987 filed Sep. 7, 2004.
Co-pending U.S. Appl. No. 10/182,830 filed Apr. 4, 2005.
Co-pending U.S. Appl. No. 10/182,830 filed Aug. 24, 2004.
Co-pending U.S. Appl. No. 10/198,931 filed Dec. 18, 2003.
Co-pending U.S. Appl. No. 10/198,931 filed Sep. 1, 2004.
Co-pending U.S. Appl. No. 10/203,018 filed May 19, 2004.
Co-pending U.S. Appl. No. 10/203,254 filed Apr. 22, 2005.
Co-pending U.S. Appl. No. 10/203,375, filed May 13, 2005.
Co-pending U.S. Appl. No. 10/312,083 filed Apr. 18, 2005.
Co-pending U.S. Appl. No. 10/312,083 filed Oct. 1, 2004.
Co-pending U.S. Appl. No. 10/413,217 filed Sep. 9, 2004.
Co-pending U.S. Appl. No. 10/699,780 filed Sep. 22, 2004.
Co-pending U.S. Appl. No. 10/699,780, filed Jun. 15, 2005.
Co-pending U.S. Appl. No. 10/746,612 filed Sep. 20, 2004.
Co-pending U.S. Appl. No. 10/746,612 filed Jun. 15, 2005.
Co-pending U.S. Appl. No. 10/787,440 filed Aug. 24, 2004.
Co-pending U.S. Appl. No. 10/787,441 filed Apr. 5, 2005.
Origins Full StoryTM Lush lash mascara product packaging, believed to have first been sold in 2003.
P. Terech, "Low-Molecular Weight Organogelators," in Specialist Surfactants, ch. 8, pp. 208-268 (I.D. Robb, ed., 1997).
Partial International Search Report in PCT/US 01/47497 filed Nov. 15, 2002.
Patent Abstracts of Japan of 2/207014.
PCT Application No. PCT/FR01/03962; Title: Composition Comprising at Least One Heteropolymer and at Least One Inert Filler and Methods for Use Inventors: Véronique Ferrari et al. International Filing Date: Dec. 12, 2001.
PCT Application No. PCT/FR01/03963; Title: Cosmetic Compositions Containing at Least One Heteropolymer and at Least One Gelling Agent and Methods of Using the Same Inventor: Véronique Ferrari International Filing Date: Dec. 12, 2001.
PCT Application No. PCT/FR01/03965; Title Cosmetic Composition Comprising Hetero Polymers and a Solid Substance and Method of Using Same Inventors: Roberto Cavazzuti et al. International Filing Date: Dec. 12, 2001.
PCT Application No. PCT/IB00/02000; Title: Composition Comprising at Least One Hetero Polymer and at Least One Inert Filler and Methods for Use Inventors: Véronique Ferrari et al. International Filing Date: Dec. 12, 2000.
PCT Application No. PCT/IB00/02006; Title: Cosmetic Compositions Containing at Least One Heteropolymer and at Least One Gelling Agent and Methods of Using the Same Inventor: Véronique Ferrari International Filing Date:Dec. 12, 2000.
PCT Application No. PCT/IB01/02780; Title:Composition Structured With a Polymer Containing a Heteroatom Organogelator International Filing Date: Dec. 12, 2001.
PCT Application No. PCT/US00/33596; Title Cosmetic Composition Comprising Hetero Polymers and a Solid Substance and Method of Using Same Inventors: Roberto Cavazzutti et al. International Filing Date: Dec. 12, 2000.
PCT Application No. PCT/US01/47454; Title: Compositions Containing Heteropolymers and Oil-Soluble Polymers and Methods of Using Same Inventors: Carlos Pinzon and Paul Thau U.S. Filing Date: Dec. 12, 2001.
PCT Application No. PCT/US01/47459; Title: Cosmetic Compositions Containing at Least One Hetero Polymer and At Least One Film-Forming Silicone Resin and Methods of Using Inventors: Mohamed Kanji et al. U.S. Filing Date: Dec. 12, 2001.
PCT Application No. PCT/US01/47496; Title: Compositions Containing Heteropolymers and Methods of Using Same Inventors: Carlos Pinzon and Paul Thau U.S. Filing Date: Dec. 12, 2001.

PCT Application No. PCT/US01/47497; Title: Compositions Containing Heteropolymers and Oil-Soluble Esters and Methods of Using Same Inventors: Carlos Pinzon and Paul Thau U.S. Filing Date: Dec. 12, 2001.

PCT Application No. PCT/US01/47499; Title: Cosmetic Compositions Containing Heteropolymers and Oil-Soluble Cationic Surfactants and Methods of Using Same Inventors: Carlos Pinzon and Paul Thau U.S. Filing Date: Dec. 12, 2001.

PCT Application No. PCT/US03/41618; Title: Cosmetic Compositions Comprising a Structuring Agent, Silicone Powder and Swelling Agent Inventors: Shao Xiang Lu, Terry Van Liew, Nathalie Geffroy-Hyland International Filing Date: Dec. 22, 2003.

PCT Application No. PCT/US04/01071; Title: Long Wear Cosmetic Composition Inventor: Balanda ATIS International Filing Date: Jan. 16, 2004.

Richard J. Lewis, Sr., "Ricinoleic Acid," Hawley's Condensed Chemical Dictionary 972 (13th. 1997).

Toshimi Shimizu et al., Stereochemical Effect of Even-Odd Connecting Links on Supramolecular Assemblies Made of 1-Glucosamide Bolaamphiphiles, J. Am Chem. Soc. 1997, 119, 2812-2818.

U.S. District Court for the District of New Jersey Civil Docket for L'Oreal S.A. et al. v. Estee Lauder Companies, Inc., et al., Civ. No. 04-1660 (HAA) (filed Apr. 7, 2004) (retrieved Jan. 2, 2005).

Xuzhong Luo et al., Self-assembled organogels formed by monoalkyl derivatives of oxamide, 2000 Chem. Commun. 2091-92.

Yasuda et al., Novel Low-molecular-weight Organic Gels: N, N', N"-Tristearyltrimesamide/Organic Solvent System, Chemistry Letters, pp. 575-576, 1996, the month of publication is not available.

* cited by examiner

COLORED TRANSPARENT OR TRANSLUCENT COSMETIC COMPOSITION

The present invention relates to transparent or translucent cosmetic compositions capable of depositing a color on the skin, lips or superficial body growths, and to a process for preparing them.

The contribution of color to the skin, the lips and superficial body growths, in particular the hair, nails and eyelashes, has always been an important subject of research in the cosmetics field and very particularly in the field of make-up.

This contribution of color is generally carried out in the form of white or colored pigments, optionally in combination with dyes, in cosmetic bases giving rise to covering colored coats (lipstick, mascara, eye shadow, eyeliner, nail varnish, foundation) or semitransparent colored coats (foundation, eye shadow, lipstick, nail varnish), the desired effect generally being the production of an intense color or the masking of underlying imperfections.

In the field of foundations, for example, the masking of skin imperfections by covering or semicovering products is, however, virtually always accompanied, despite the application as a very fine layer, by a degree of visibility of the coat and by an unnatural appearance, which is generally undesirable.

Furthermore, there exist cosmetic compositions, such as care creams, which, after application as a fine layer, are entirely transparent or else sufficiently translucent (see WO 98/5234) to retain the natural appearance of the skin and to only lightly mask the imperfections of the latter. However, these products do not make it possible to color the physiological substrate on which they are deposited.

The inventors set a target of developing a novel range of noncovering make-up products which make it possible to deposit a color on the skin, lips or superficial body growths while remaining entirely "invisible", that is to say products capable of giving coats which are sufficiently transparent or translucent to retain the natural appearance of the underlying surface.

A subject matter of the present invention is consequently transparent or translucent colored cosmetic compositions for making up the skin, lips and superficial body growths comprising a bulk transparent or translucent cosmetic base and at least one coloring agent in an amount such that the transmission of a 10 µm layer of the final composition, measured at the wavelength of the maximum of one of the absorption or scattering peaks of the coloring agent, is between 20% and 80%.

Another subject matter of the invention is a process for the preparation of a transparent or translucent colored cosmetic composition described above.

The cosmetic compositions which are a subject matter of the present invention thus make it possible to color the substrate on which they are applied while giving, by virtue of the high "transparency" of the coat obtained, a perfectly natural appearance to the surface thus covered.

The colored cosmetic compositions of the present invention have, as characteristic, not only the coloring capability and the transparency of the coat obtained but also a "bulk" transparent or translucent appearance. This property of bulk transparency or translucency means that a layer with a thickness arbitrarily set at 1 cm allows a portion of the visible light to pass through, either while scattering it (bulk translucent compositions) or without scattering it (bulk transparent compositions).

This transparent or translucent appearance is highly satisfactory from an esthetic viewpoint and can for this reason be of great commercial interest.

The cosmetic compositions of the present invention are characterized in that they have a transmission at a thickness of 10 µm, measured at the wavelength of the maximum of one of the absorption or scattering peaks of the coloring agent, of between 20% and 80%.

This layer thickness of 10 µm at which the measurements of transmission of the compositions of the present invention are carried out was chosen because it corresponds substantially to the thickness of a make-up coat obtained, for example, with a foundation or a lipstick. The values obtained by these measurements therefore give a good description of what is commonly known as "make-up rendering", that is to say of the immediate visual impression which the make-up layer gives.

The transmission as defined here is equal to the ratio of the intensity of light transmitted by the sample ($I_t$) to the intensity of light transmitted by the control ($I_0$), express as a %:

$$T(\%) = I_t/I_0$$

The inventors use specific sample carriers in order to be able to carry out measurements over a layer thickness of 10 µm.

They consist of a transparent glass or quartz slide, the size of which depends on the measuring cell of the spectrophotometer used (20 mm×10 mm×3 mm for a Cary 300), exhibiting at its surface a flat recess with a depth of 10 µm. This flat recess is filled with the sample and the excess is optionally leveled down using a slide, so as thus to obtain a perfectly even layer with a thickness of 10 µm.

The measurements are carried out using a double-beam UV/visible spectrophotometer, Cary 300 model from Varian, in transmission mode and by using, as control, a transparent slide (of quartz or of glass) with an identical thickness to that receiving the sample.

As indicated above, the transmission values indicated for the compositions according to the invention are those measured at the wavelength corresponding to the maximum of one of the absorption peaks (dye) or scattering peaks (pigment) of the coloring agent in the visible light region ($\lambda = 400$ to 750 nm).

The error in the measurement of the transmission is ±5%.

The "bulk" transparency or translucency of the colored cosmetic compositions of the present invention is evaluated visually for a layer thickness of 1 cm.

The transparent or translucent colored cosmetic compositions are obtained by virtue of the combination of:
  (1) a bulk transparent or translucent cosmetic base, and
  (2) at least one appropriate coloring agent.

The cosmetic bases which can be used for the preparation of the compositions of the present invention can be composed of any cosmetically acceptable base which meets the conditions of transparency or of translucency essential for the production of the transparent or translucent colored cosmetic compositions.

These conditions of transparency or of translucency are:
  (1) good bulk transparency or translucency of the colorant-free base, assessed visually for a thickness of 1 cm, and
  (2) a transmission of the base comprising the colorant or colorants measured for a thickness of
    10 µm at the wavelength of the maximum of one of the absorption or scattering peaks of the coloring agent used of between 20% and 80%.

good bulk transparency or translucency of the colorant-free base, assessed visually for a thickness of 1 cm, and a transmission of the base comprising the colorant or colorants, measured for a thickness of 10 μm at the wavelength of the maximum of one of the absorption or scattering peaks of the coloring agent used, of between 20% and 80%.

It can relate to hydrophilic or lipophilic phases with a liquid, thickened, gelled, pasty or solid consistency.

Preferably, the base of the composition is in the form of an aqueous or oily gel which is more or less rigid. More especially, this gel is a rigid gel presented in a dish or as a stick, preferably as a stick, and in the anhydrous form. In particular, this base is an anhydrous foundation or lipstick base.

The oily base comprises a fatty phase which is liquid at ambient temperature, such as those used conventionally in cosmetics. This fatty phase can comprise polar oils and/or nonpolar oils.

In particular, the polar oils of the invention are:
(1) hydrocarbonaceous vegetable oils with a high content of triglycerides composed of esters of fatty acids and of glycerol, the fatty acids of which can have various $C_4$ to $C_{24}$ chain lengths, it being possible for these chains to be linear or branched and saturated or unsaturated; these oils are in particular wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, passionflower or musk rose oil; or triglycerides of caprylic/capric acid, such as those sold by Stearineries Dubois or those sold under the names Miglyol 810, 812 and 818 by Dynamit Nobel;
(2) synthetic oils or synthetic esters of formula $R_aCOOR_b$ in which $R_a$ represents the residue of a linear or branched fatty acid comprising from 1 to 40 carbon atoms and $R_b$ represents a hydrocarbonaceous chain, in particular a branched hydrocarbonaceous chain, comprising from 1 to 40 carbon atoms, provided that $R_a+R_b$ is $\geq 10$ such as, for example, purcellin oil (cetostearyl octanoate), isononyl isononanoate, $C_{12}$ to $C_{15}$ alkyl benzoate, isopropyl myristate, 2-ethylhexyl palmitate, isostearyl isostearate, or octanoates, decanoates or ricinoleates of alcohols or of polyalcohols; hydroxylated esters, such as isostearyl lactate or diisostearyl malate; and pentaerythritol esters;
(3) synthetic ethers having from 10 to 40 carbon atoms;
(4) $C_8$ to $C_{26}$ fatty alcohols, such as oleyl alcohol;
(5) $C_8$ to $C_{26}$ fatty acids, such as oleic acid, linolenic acid and linoleic acid; and
(6) mixtures thereof.

The nonpolar oils according to the invention are in particular silicone oils, such as volatile or nonvolatile and linear or cyclic polydimethylsiloxanes (PDMS) which are liquid at ambient temperature; polydimethylsiloxanes comprising alkyl or alkoxy side groups and/or alkyl or alkoxy groups at the chain end, which groups each have from 2 to 24 carbon atoms; phenylated silicones, such as phenyl trimethicones, phenyl dimethicones, phenyltrimethylsiloxydiphenylsiloxanes, diphenyl dimethicones, diphenylmethyldiphenyltrisiloxanes or (2-phenylethyl)trimethylsiloxysilicates; volatile or nonvolatile and linear or branched hydrocarbons of synthetic or mineral origin, such as volatile liquid paraffins (isoparaffins, such as isododecane) or nonvolatile liquid paraffins, and their derivatives, liquid petrolatum, liquid lanolin, polydecenes, hydrogenated polyisobutene, such as parleam oil, squalane or arara oil; and their mixtures.

The oils are preferably nonpolar oils and more especially an oil or a mixture of oils of the hydrocarbonaceous type of mineral or synthetic origin chosen in particular from alkanes, such as parleam oil, isoparaffins, such as isododecane, squalane and their mixtures. These oils are advantageously used in combination with one or more phenylated silicone oils.

The liquid fatty phase preferably comprises at least one nonvolatile oil chosen in particular from hydrocarbonaceous oils of mineral, vegetable or synthetic origin, synthetic esters or ethers, silicone oils and their mixtures.

The total liquid fatty phase represents, in practice, from 5 to 99.95%, preferably from 10 to 80%, and more preferably from 20 to 75%, of the total weight of the composition.

This fatty phase is advantageously structured by a gelling agent for fatty phases, such as:
(1) gelling polyamides, in particular with a molecular mass of less than 100 000, and preferably less than 50 000, for example with a molecular mass ranging from 2 000 to 20 000, optionally comprising alkyl side groups or alkyl groups at the chain end having from 8 to 120 carbon atoms, and preferably from 12 to 60 carbon atoms,
(2) hydrophobic galactomannans comprising in particular from 1 to 6, and preferably from 2 to 4, OH groups per monosaccharide unit which are substituted by a $C_{1-6}$, preferably $C_{1-3}$, alkyl group,
(3) hydrophobic pyrogenic silicas,
(4) and the combinations of these gelling agents.

The gelling polyamides are, for example, the polyamide resins resulting from the condensation of an aliphatic dicarboxylic acid and of a diamine, including the compounds having more than 2 carboxyl groups and more than 2 amine groups, the carboxyl and amine groups of adjacent individual units being condensed by an amide bond. These polyamide resins are in particular those sold under the Versamid® trademark by General Mills Inc. and Henkel Corp. (Versamid® 930, 744 or 1655) or by Olin Mathieson Chemical Corp. under the Onamid® trademark, in particular Onamid® S or C. These resins have a weight-average molecular mass ranging from 6 000 to 9 000. For further information on these polyamides, reference may be made to U.S. Pat. Nos. 3,645,705 and 3,148,125. More specifically, use is made of Versamid® 930 or 744.

Use may also be made of the polyamides sold by Arizona Chemical under the Uni-Rez references (2658, 2931, 2970, 2621, 2613, 2624, 2665, 1554, 2623, 2662) and the product sold under the reference Macromelt 6212 by Henkel. For further information on these polyamides, reference may be made to U.S. Pat. No. 5,500,209.

The polyamides can also be those resulting from a polycondensation between a carboxylic diacid comprising at least 32 carbon atoms (in particular from 32 to 44 carbon atoms) and a diamine having at least 2 carbon atoms (in particular from 2 to 36 carbon atoms). The diacid is preferably a dimer of a fatty acid having at least 16 carbon atoms, such as oleic, linoleic or linolenic acid. The diamine is preferably ethylenediamine, hexylenediamine or hexamethylenediamine. If the polymers comprise one or two end carboxylic acid groups, it is advantageous to esterify them with a monoalcohol having at least 4 carbon atoms, preferably from 10 to 36 carbon atoms, more preferably from 12 to 24 carbon atoms, and even more preferably from 16 to 24 carbon atoms, for example, 18 carbon atoms.

These polymers are more especially those disclosed in U.S. Pat. No. 5,783,657 of Union Camp. Each of these polymers satisfies in particular the following formula (I):

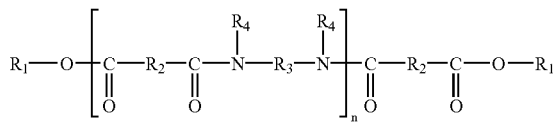

in which n denotes a whole number of amide units such that the number of ester groups represents from 10% to 50% of the total number of the ester and amide groups; each of the $R_1$ symbols independently denotes an alkyl or alkenyl group having at least 4 carbon atoms and in particular from 4 to 24 carbon atoms; each of the $R_2$ symbols independently represents a $C_4$ to $C_{42}$ hydrocarbonaceous group, provided that 50% of the $R_2$ groups represent a $C_{30}$ to $C_{42}$ hydrocarbonaceous group; each of the $R_3$ symbols independently represents an organic group provided with at least 2 carbon atoms, with hydrogen atoms and optionally with one or more oxygen or nitrogen atoms; and each of the $R_4$ symbols independently represents a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

In the specific case of the formula (I), the optionally functionalized end fatty chains within the meaning of the invention are end chains bonded to the final heteroatom, in this instance nitrogen, of the polyamide backbone.

In particular, the ester groups of the formula (I), which form part of the end and/or side fatty chains within the meaning of the invention, represent from 15 to 40% of the total number of the ester and amide groups, and more preferably from 20 to 35%. Furthermore, n advantageously represents an integer ranging from 1 to 5, and preferably of greater than 2.

Preferably, $R_1$ is a $C_{12}$ to $C_{22}$ alkyl group and more preferably a $C_{16}$ to $C_{22}$ alkyl group. Advantageously, $R_2$ can be a $C_{10}$ to $C_{42}$ hydrocarbonaceous (alkylene) group. Preferably, at least 50%, and more preferably at least 75%, of the $R_2$ symbols are groups having from 30 to 42 carbon atoms. The other $R_2$ symbols are $C_4$ to $C_{19}$ and even $C_4$ to $C_{12}$ hydrogenated groups. Preferably, $R_3$ represents a $C_2$ to $C_{36}$ hydrocarbonaceous group or a polyoxyalkylene group and $R_4$ represents a hydrogen atom. More preferably, $R_3$ represents a $C_2$ to $C_{12}$ hydrocarbonaceous group.

The hydrocarbonaceous groups can be linear, cyclic or branched and saturated or unsaturated groups. Furthermore, the alkyl and alkylene groups can be linear or branched and saturated or unsaturated groups.

According to the invention, the structuring of the liquid fatty phase is preferably obtained using one or more polymers of formula (I). In general, the polymers of formula (I) are provided in the form of blends of polymers, it being possible for these blends to additionally comprise a synthetic product corresponding to a compound of formula (I) where n has the value 0, that is to say a diester.

These polymers, because of their fatty chain(s), exhibit good solubility in oils and thus result in macroscopically homogeneous compositions, even with a high (at least 25%) level of polymer, in contrast to polymers devoid of a fatty chain.

Mention may be made, as preferred structuring polymers of formula (I) which can be used in the invention, of the polyamides modified by side fatty chains and/or end fatty chains having from 8 to 120 carbon atoms, and in particular from 12 to 68 carbon atoms, the end fatty chains being bonded to the polyamide backbone via ester groups. These polymers preferably comprise a fatty chain at each end of the polymer backbone and in particular of the polyamide backbone.

Mention may be made, as examples of structuring polyamides of formula (I) which can be used in the composition according to the invention, of the commercial products sold by Arizona Chemical under the names Uniclear® 80 and Uniclear® 100. They are sold respectively in the form of an 80% (as active material) gel in a mineral oil and of a 100% (as active material) gel. They have a softening point of 88 to 94° C. These commercial products are a blend of copolymers of a $C_{36}$ diacid condensed with ethylenediamine, with a weight-average molecular mass respectively of approximately 600 or 4 000. The end ester groups result from the esterification of the remaining acid endings with cetyl alcohol or stearyl alcohol or their mixtures (also known as cetearyl alcohol).

The galactomannans are in particular ethylated guar derivatives having especially a degree of substitution of 2 to 3, such as those sold by Aqualon under the names N-Hance-AG-200® or N-Hance-AG-50®.

The pyrogenic silica preferably exhibits a particle size which can be nanometric to micrometric, for example ranging from approximately from 5 to 200 nm.

Pyrogenic silicas can be obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces. Such hydrophilic silicas are, for example, sold under the names Aerosil 130®, Aerosil 200®, Aerosil 255®, Aerosil 300® and Aerosil 380® by Degussa or under the names Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica by a chemical reaction which reduces the number of silanol groups. It is possible in particular to substitute silanol groups by hydrophobic groups and thus to obtain a hydrophobic silica. The hydrophobic groups can be:

(1) trimethylsiloxy groups, which are obtained in particular by treatment of pyrogenic silica in the presence of hexamethyldisilazane and are named "Silica silylate" according to the CTFA (6th edition, 1995); they are sold, for example, under the name Aerosil R812® by Degussa and under the name Cab-O-Sil TS-530® by Cabot;

(2) dimethylsilyloxy or polydimethylsiloxane groups, which are obtained in particular by treatment of pyrogenic silica in the presence of polydimethylsiloxane or of dimethyldichlorosilane and are named "Silica dimethyl silylate" according to the CTFA (6th edition, 1995); they are sold, for example, under the names Aerosil R972® and Aerosil R974® by Degussa and under the names Cab-O-Sil TS-610® and Cab-O-Sil TS-720® by Cabot; and (3) groups resulting from the reaction of the pyrogenic silica with alkoxysilanes or siloxanes; these treated silicas are, for example, those sold under the reference Aerosil R805® by Degussa.

When the gel is an aqueous gel, use may be made of any gelling agent for aqueous phases of the cellulose derivative type, such as hydroxyethylcellulose and carboxymethylcellulose, or acrylic derivative type, such as crosslinked copolymers of acrylic acid and of $C_{10-30}$ alkyl acrylates, for example the Pemulen® series and Carbopol® 980, which are sold by Goodrich, clay derivatives of the sodium magnesium silicate type, such as Laponite XLS or XLG, sold by Laporte, and the combinations of these gelling agents. The aqueous gel can be a water-based gel or a gel based on a water/alcohol mixture.

The gelling agent represents from 0.05 to 90% by weight, preferably from 2 to 60% by weight, and more preferably from 5 to 40% by weight, of the total weight of the colored cosmetic composition.

The transparent or translucent cosmetic bases used according to the invention are preferably substantially colorless.

One or more coloring agents is introduced, according to the present invention, into these transparent or translucent cosmetic bases.

According to the present invention, the term "coloring agent" encompasses in particular water-soluble or fat-soluble dyes, pigments, pearlescence agents, lakes and their mixtures.

Mention may be made, as water-soluble dyes, of synthetic dyes, such as fuchsin, plant extracts, such as extracts of sorghum, of *Pterocarpus soyauxii*, of *Monascus*, of *Lawsonia inermis*, of *Mercurialis perenis*, of *Helianthus aanus*, of *Impatiens balsamina*, of *Curcuma longa*, of *Phytolacca decandra*, of *Solidago aureus*, of *Juglans regia*, of *Iris germanica*, of *Alkanna tinctoria*, of *Chrozophoro tinctoria* or of *Isatis tinctoria*, and the mixtures of these dyes.

The fat-soluble dyes are, for example, Sudan red III (CTFA: D&C Red 17), lutein, quinizarin green (CTFA: D&C Green 6), alizurol purple SS (CTFA: D&C Violet No. 2), carotenoid derivatives, such as lycopene, β-carotene, bixin or capsantein, annatto and fuchsin derivatives (see Example 2), and their mixtures.

A number of these dyes, such as extracts of *Pterocarpus soyauxii*, *Monascus* and *Lawsonia inermis*, have a strong affinity for the skin and can thus confer a semipermanent coloring thereon, that is to say a coloring which withstands being washed several times.

The term "pigments" should be understood as meaning white or colored, inorganic or organic and coated or uncoated particles. Mention may be made, for example, of titanium, zirconium or cerium dioxides, zinc, iron or chromium oxides, ferric blue, chromium hydrate, carbon black, ultramarines (polysulfides of aluminum silicates), manganese violet, manganese pyrophosphate and some metal powders, such as silver or aluminum powders, and their mixtures.

The term "pearlescence agents" is understood to mean white nacreous pigments, such as mica covered with titanium oxide or with bromuth oxychloride, and colored nacreous pigments, such as titanium oxide-coated mica covered with iron oxides, ferric blue or chromium oxide or with a precipitated typical organic pigment.

The lakes which can be used in the compositions of the present invention are, for example, lakes based on cochineal carmine or based on calcium, barium, aluminum, strontium or zirconium salts, on acid dyes, and their mixtures.

The amount of coloring agent is determined for the present invention. This is because this amount directly determines the transmission of the composition, which, for a thickness of 10 μm, has to be between 20% and 80% at the wavelength corresponding to the maximum of one of the absorption or scattering peaks of the coloring agent.

Below a certain amount of coloring agent (transmission at 10 μm of greater than 80%), the composition will give rise to a coat which is sufficiently transparent or translucent to retain the natural appearance of the skin, lips or superficial body growths but it will not allow a coloring visible to the naked eye to be introduced.

On the other hand, for an excessively high proportion of coloring agent (transmission at 10 μm of less than 20%), the color of the make-up coat will certainly be visible but the transparency or the translucency of the latter will be insufficient to retain the natural appearance of the skin. Furthermore, cosmetic compositions comprising an excessively high proportion of coloring agent will exhibit unsatisfactory bulk transparency or translucency.

In a preferred embodiment of the invention, the colored cosmetic compositions have a transmission, measured for a thickness of 10 μm, at the wavelength corresponding to the maximum of one of the absorption or scattering peaks of the coloring agent, of between 25% and 80%.

The process for determining the appropriate amount of coloring agent which makes it possible to obtain transparent or translucent colored compositions according to the present invention will be described in more detail below.

The appropriate amount of coloring agent will obviously depend on its physicochemical properties, such as its solubility in the cosmetic base, its particle size or its molar coefficient of absorption ($\epsilon$).

The transparent or translucent colored cosmetic compositions according to the present invention generally comprise from 0.05% to 3% by weight, and preferably from 0.1 to 1% by weight, of coloring agent(s), on the basis of the total weight of the colored cosmetic composition. For the pearlescence agents, it is possible to range up to 3% by weight; for the pigments, the lakes or the dyes, the range preferably only extends up to 1% by weight.

In a preferred embodiment of the present invention, the colored cosmetic composition comprises at least one water-soluble or fat-soluble dye which is soluble in the cosmetic base.

In another particularly advantageous embodiment of the invention, the colored cosmetic composition comprises, as coloring agent(s), solely one or more dyes which are soluble in the cosmetic base and is devoid of insoluble coloring agents of pigment, pearlescence agent or lake type.

In a more particularly preferred embodiment of the present invention, the cosmetic base is a lipophilic base comprising one or more lipophilic dyes which are soluble in the latter.

This is because such compositions, comprising solely soluble dyes, have a good coloring power in combination with excellent transparency properties due to the absence of scattering of the light by insoluble particles.

Another subject matter of the present invention is a process for the preparation of the transparent or translucent colored cosmetic compositions of the present invention which has, as main characteristics:

(1) choosing an appropriate transparent or translucent cosmetic base, and (2) apportioning the coloring agent(s), that is to say the incorporation of an appropriate amount of coloring agent(s) which makes it possible to solve the technical problem at the source of the invention, that is to say the production of a colored coat having a transmission (at 10 μm and at $\lambda_{max}$) of between 20% and 80%.

The determination of the appropriate amount of coloring agent comprises the steps consisting of:
(1) selecting a transparent or translucent cosmetic base as described above,
(2) preparing a series of samples of this transparent or translucent cosmetic base comprising increasing amounts of a coloring agent dissolved or dispersed in said cosmetic base,
(3) spreading each of the samples thus prepared over a transparent slide exhibiting a recess with a depth of 10 μm,
(4) optionally leveling out the excess of the sample, so as to obtain a layer with a thickness of 10 μm,
(5) measuring, for each of the samples, the transmission of said layer at the wavelength corresponding to the maximum of one of the absorption or scattering peaks of the coloring agent, and
(6) plotting the transmission=f(concentration of the coloring agent) calibration curve.

Colored cosmetic compositions are subsequently prepared by incorporating one or more coloring agents in a transparent or translucent cosmetic base which is identical to or different than that selected in step (1) above and which is in the liquid state, each of the coloring agents being incorporated in an amount giving, from the calibration curve prepared for each coloring agent, a transmission (at 10 μm) of between 20% and 80%, preferably between 25% and 80%.

To receive the coloring agent, the cosmetic base must, of course, be in the liquid state. The liquid consistency can be a property of the base as such at ambient temperature or it can be the result of the melting or dissolution of a cosmetic base which is solid at ambient temperature.

The solid anhydrous cosmetic bases preferred according to the present invention are preferably liquefied by melting at a temperature slightly above their melting point.

The present invention is illustrated by the following examples:

EXAMPLE 1

| Lipstick | |
| --- | --- |
| Uniclear ® 100 | 25% |
| Octyldodecanol | 10% |
| Rocou ® | 0.2% |
| | (coloring active material) |
| Parleam oil | q.s. for 100% by weight |

Uniclear ® 100: condensate of a hydrogenated $C_{36}$ diacid and of ethylenediamine esterified with stearyl alcohol (weight-average molar mass approximately 4 000), sold by Arizona Chemical.
Rocou ®: 4% solution of annatto seeds in soybean oil (CI: 75120), sold by Warner-Jenkinson.

The Uniclear® 100 and the oils are introduced into a casserole. The combined contents are stirred magnetically and are heated in a first step to 100° C. to bring the Uniclear to the liquid state. Heating is then continued as far as the temperature necessary to produce a homogeneous transparent liquid. The mixture is then placed at 10° C. above this temperature. The dye is introduced into the mixture and the combined contents are homogenized with magnetic stirring for 1 hour. The composition is cast in a mold heated at 45° C. to form a stick which is placed, after solidification has begun, in a freezer for 15 minutes (−21° C.).

The composition obtained has a bulk translucent appearance (1 cm) and gives rise to a completely transparent coat with an orange color having a transmission at 498 nm ($\lambda_{max}$ of the dye) and at a thickness of 10 μm of 78%.

EXAMPLE 2

| Lipstick | |
| --- | --- |
| Uniclear ® 100 | 25% |
| Octyldodecanol | 10% |
| MMB Red ® 33/3 complex | 0.2% |
| | (coloring active material) |
| Parleam oil | q.s. for 100% by weight |

Uniclear ® 100: condensate of a hydrogenated $C_{36}$ diacid and of ethylenediamine esterified with stearyl alcohol (weight-average molar mass approximately 4 000), sold by Arizona Chemical.
MMB Red ® 33/3 complex: dye sold under this name by Phytocos and denoting the mixture: disodium salt of fuchsin acid D/lysine palmitate-myristate/dipropylene glycol/benzoic acid/phenoxyethanol/3% solution of D&C Red No. 33 (CI 17200)/preservatives: methyl, butyl, ethyl, propyl p-hydroxybenzoate.

A stick is prepared by the same process as in Example 1.
The composition obtained has a bulk translucent appearance (1 cm) and gives rise to a completely transparent coat with a fuchsia pink color having a transmission at 530 nm ($\lambda_{max}$ of the dye) and at a thickness of 10 μm of 40%.

The invention claimed is:

1. A transparent or translucent colored cosmetic composition for making up at least one of skin, lips and superficial body growths, comprising a bulk transparent or translucent cosmetic base and at least one coloring agent in an amount such that the transmission of a 10 μm layer of said cosmetic composition measured at the wavelength of the maximum of the absorption or scattering peak of the at least one coloring agent ranges from 20% to 80%.

2. The colored cosmetic composition according to claim 1, wherein the transparent or translucent cosmetic base is a substantially colorless base.

3. The colored cosmetic composition according to claim 1, wherein the cosmetic base is chosen from aqueous gels and oily gels.

4. The colored cosmetic composition according to claim 3, wherein the gel is in stick form.

5. The colored cosmetic composition according to claim 1, wherein the base is an anhydrous gel formed from a fatty phase which is liquid at ambient temperature comprising an oil chosen from polar oils and nonpolar oils, wherein the fatty phase is structured by a gelling agent for fatty phases which is chosen from at least one of hydrophobic pyrogenic silicas, gelling polyamides, and hydrophobic galactomannans.

6. The colored cosmetic composition according to claim 5, wherein the gelling polyamide corresponds to the formula (I):

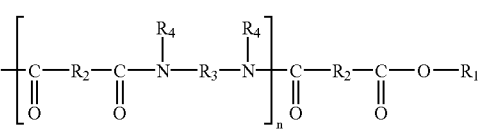

in which n represents a whole number such that the number of ester groups ranges from 10% to 50% of the total number of the ester and amide groups;

$R_1$, which may be identical or different, represents a group chosen from alkyls having at least 4 carbon atoms and alkenyls having at least 4 carbon atoms;

$R_2$, which may be identical or different, represents a $C_4$ to $C_{42}$ hydrocarbonaceous group, provided that 50% of the $R_2$ groups represent a $C_{30}$ to $C_{42}$ hydrocarbonaceous group;

$R_3$, which may be identical or different, represents an organic group having at least 2 carbon atoms, hydrogen atoms, and optionally at least one atom chosen from oxygen atoms and nitrogen atoms; and $R_4$, which may be identical or different, represents a group chosen from hydrogen atoms, $C_1$ to $C_{10}$ alkyls, optionally directly bonded to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

7. The colored cosmetic composition according to claim 6, wherein $R_1$, which may be identical or different, represents a group chosen from alkyls having 4 to 24 carbon atoms and alkenyls having 4 to 24 carbon atoms.

8. The colored cosmetic composition according to claim 1, wherein the at least one coloring agent is chosen from at least one of water-soluble dyes, fat-soluble dyes, pigments, pearlescence agents, and lakes.

9. The colored cosmetic composition according to claim 8, wherein the water-soluble dye is chosen from at least one of extracts of sorghum, *Pterocarpus soyauxii, Monascus, Lawsonia inermis, Mercurialis perenis, Helianthus aanus, Impatiens balsamina, Curcuma longa, Phytolacca decandra, Solidago aureus, Juglans regia, Iris germanica, Alkanna tinctoria, Chrozophoro tinctoria*, and *Isatis tinctoria*.

10. The colored cosmetic composition according to claim 8, wherein the fat-soluble dye is chosen from at least one of Sudan red III, lutein, quinizarin green, alizural purple SS, carotenoid derivatives, annatto derivatives, and fuchsin derivatives.

11. The colored cosmetic composition according to claim 10, wherein the carotenoid derivative is chosen from lycopene, β-carotene, bixin, and capsantein.

12. The colored cosmetic composition according to claim 8, wherein the pigment is chosen from at least one of white inorganic pigments, colored inorganic pigments, white coated inorganic pigments, colored coated inorganic pigments, white organic pigments, and colored organic pigments.

13. The colored cosmetic composition according to claim 12, wherein the pigment is chosen from at least one of titanium dioxide, zirconium dioxide, cerium dioxide, zinc oxide, iron oxide, chromium oxide, ferric blue, chromium hydrate, carbon black, ultramarines, manganese violet, manganese pyrophosphate, and metal powders.

14. The colored cosmetic composition as claimed in claim 13, wherein the metal powder is chosen from silver powders and aluminum powders.

15. The colored cosmetic composition according to claim 8, wherein the pearlescence agent is chosen from mica covered with at least one of titanium oxide and bismuth oxychloride and titanium oxide-coated mica covered with at least one of iron oxide, ferric blue, chromium oxide, and precipitated organic pigments.

16. The colored cosmetic composition according to claim 8, wherein the lake is chosen from at least one of lakes based on cochineal carmine, lakes based on at least one of calcium salts, barium salts, aluminum salts, strontium salts, and zirconium salts, and lakes based on acid dyes.

17. The colored cosmetic composition according to claim 8, wherein the composition comprises at least one dye chosen from water-soluble dyes and fat-soluble dyes, wherein the dye is soluble in the cosmetic base.

18. The colored cosmetic composition according to claim 17, wherein the composition comprises, as the at least one coloring agent, at least one dye which is soluble in the cosmetic base and wherein the composition is devoid of insoluble coloring agents chosen from pigments, pearlescence agents, and lakes.

19. The colored cosmetic composition according to claim 17, wherein the cosmetic base is a lipophilic base and wherein the composition comprises at least one lipophilic dye which is soluble in the lipophilic base.

20. The colored cosmetic composition according to claim 1, wherein the at least one coloring agent is present in an amount such that the transmission of the 10 μm layer of the composition measured at the wavelength of the maximum of the absorption or scattering peak of the at least one coloring agent ranges from 25% to 80%.

21. The colored cosmetic composition according to claim 1, wherein the amount of the at least one coloring agent ranges from 0.05% to 3% by weight with respect to the total weight of the composition.

22. The colored cosmetic composition according to claim 1, wherein the amount of the at least one coloring agent ranges from 0.1% to 1% by weight with respect to the total weight of the composition.

23. The colored cosmetic composition according to claim 1, wherein the composition is chosen from anhydrous lipstick forms and anhydrous foundation forms.

24. A process for the preparation of a transparent or translucent colored cosmetic composition for making up skin, lips and superficial body growths, comprising a bulk transparent or translucent cosmetic base and at least one coloring agent in an amount such that the transmission of a 10 μm layer of the composition measured at the wavelength of the maximum of the absorption or scattering peak of the at least one coloring agent ranges from 20% to 80%, wherein the process comprises:

(1) selecting the cosmetic base, (2) preparing a series of samples of the cosmetic base comprising increasing amounts of the at least one coloring agent dissolved or dispersed in the cosmetic base, (3) spreading each of the samples thus prepared over a translucent slide having a recess with depth of 10 μm, (4) optionally leveling the sample so as to obtain an even layer with a thickness of 10 μm, (5) measuring, for each of the samples, the transmission of the layer at the wavelength corresponding to the maximum of the absorption or scattering peak ($\lambda_{max}$) of the at least one coloring agent, (6) plotting a calibration curve wherein the values of the transmission at ($\lambda_{max}$) is a function of the concentration of the at least one coloring agent, and (7) incorporating the at least one coloring agent in a transparent or translucent cosmetic base which is identical or different from that selected in step (1) above and which is in a liquid state, the at least one coloring agent being incorporated in the cosmetic base in an amount which, according to the calibration curve prepared for each coloring agent, results in a transmission at 10 μm of ranging from 20% to 80%.

25. The process as claimed in claim 24, wherein the transmission in step (7) ranges from 25% to 80%.

* * * * *